United States Patent [19]

Wuesi et al.

[11] Patent Number: 4,714,786
[45] Date of Patent: Dec. 22, 1987

[54] VINYLPHENOL DERIVATIVES, THEIR PREPARATION AND THEIR USE

[75] Inventors: Hans-Heiner Wuesi, Dossenheim; Bernd Janssen, Ludwigshafen; Fritz-Frieder Frickel, Deidesheim; Axel Nuerrenbach, Gruenstadt, all of Fed. Rep. of Germany

[73] Assignee: BASF Aktiengesellschaft, Ludwigshafen, Fed. Rep. of Germany

[21] Appl. No.: 7,586

[22] Filed: Jan. 28, 1987

[30] Foreign Application Priority Data

Jan. 28, 1986 [DE] Fed. Rep. of Germany ....... 3602473

[51] Int. Cl.$^4$ ............................................. C07C 43/215
[52] U.S. Cl. .................................... 568/633; 524/859; 514/863; 568/631; 568/632
[58] Field of Search ............... 568/631, 632, 633, 646; 514/859, 863

[56] References Cited

U.S. PATENT DOCUMENTS 4,326,055 4/1982 Loeliger ............................. 542/429

FOREIGN PATENT DOCUMENTS 1183541 3/1985 Canada ................................. 568/633
3443231 6/1985 Fed. Rep. of Germany ...... 514/863

Primary Examiner—Werren B. Lone
Attorney, Agent, or Firm—Keil & Weinkauf

[57] ABSTRACT

Vinylphenol derivatives of the formula I

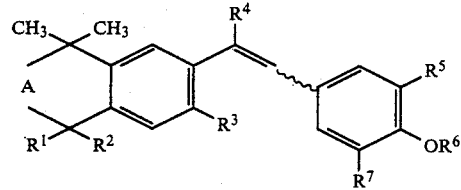

where A and $R^1$ to $R^7$ have the meanings stated in claim 1 and in the description, and their physiologically tolerated salts, drugs prepared from these, and their use for the treatment of various disorders of the skin, the mucous membranes and the internal organs, and of rheumatic disorders.

6 Claims, No Drawings

VINYLPHENOL DERIVATIVES, THEIR PREPARATION AND THEIR USE

The present invention relates to novel vinylphenol derivatives, processes for their preparation and their use for controlling disorders.

German Laid-Open Applications DOS No. 2,854,354 and DOS No. 3,202,118 disclose that vinylbenzoic acid derivatives have pharmacological actions in the topical and systemic therapy of neoplasia, acne, psoriasis and other dermatological affections. However, their action is not always satisfactory, in particular because of undesirable side effects.

We have found that vinylphenol derivatives of the formula I

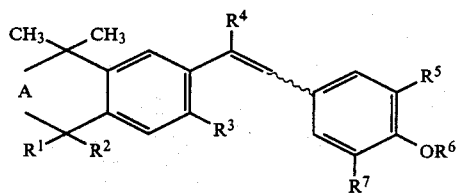

where

A is a methylene or ethylene radical which is unsubstituted or substituted by $C_1$-$C_4$-alkyl, preferably methyl, $R^1$ and $R^2$ are each hydrogen or methyl, $R^3$ is hydrogen, $C_1$-$C_4$-alkyl, $C_1$-$C_4$-alkoxy or halogen, $R^4$ is hydrogen, $C_1$-$C_4$-alkyl, cyclopropyl or cyclobutyl, $R^5$ and $R^7$ are each hydrogen or —$OR^8$, where $R^8$ is hydrogen, $C_1$-$C_4$-alkyl or $C_1$-$C_4$-alkanoyl, and $R^6$ is hydrogen or is $C_1$-$C_4$-alkyl which is unsubstituted or substituted by carboxyl, $C_1$-$C_4$-alkoxycarbonyl, hydroxyl, $C_1$-$C_4$-alkoxy and/or amino or mono- or di-$C_1$-$C_4$-alkylamino, or is $C_1$-$C_{20}$-alkanoyl or is benzoyl which is unsubstituted or substituted as described for the $C_1$-$C_4$-alkyl group, or is aralkyl which is unsubstituted or similarly substituted in the aryl moiety, and their physiologically tolerated salts have a better action spectrum coupled with lower toxicity and a higher therapeutic index.

$R^6$ and $R^8$ together may furthermore be a radical $>C=O$, $>C=S$, —$CH_2CH_2$— or $>CR^9R^{10}$, where $R^9$ and $R^{10}$ are each hydrogen, $C_1$-$C_4$-alkyl or phenyl.

Aryl is preferably phenyl, which may be substituted by methyl, methoxy or nitro. Aralkyl is preferably benzyl, which may be substituted in the aryl moiety by methyl, methoxy or halogen. Substituents of the benzoyl group can be, for example, methyl, methoxy, or halogen. Halogen atoms $R^3$ are preferably fluorine or chlorine.

Typical examples of compounds according to the invention are:

1-(4-hydroxyphenyl)-2-(5,6,7,8-tetrahydro-5,5,8,8-tetramethylnaphth-2-yl)-propene 1-(4-methoxyphenyl)-2-(5,6,7,8-tetrahydro-5,5,8,8-tetramethylnaphth-2-yl)-propene 1-(4-ethoxyphenyl)-2-(5,6,7,8-tetrahydro-5,5,8,8-tetramethylnaphth-2-yl)-propene 1-(4-propoxyphenyl)-2-(5,6,7,8-tetrahydro-5,5,8,8-tetramethylnaphth-2-yl)-propene 1-(4-butoxyphenyl)-2-(5,6,7,8-tetrahydro-5,5,8,8-tetramethylnaphth-2-yl)-propene 1-(4-isopropoxyphenyl)-2-(5,6,7,8-tetrahydro-5,5,8,8-tetramethylnaphth-2-yl)-propene 1-(4-t-butoxyphenyl)-2-(5,6,7,8-tetrahydro-5,5,8,8-tetramethylnaphth-2-yl)-propene 1-(4-formyloxyphenyl)-2-(5,6,7,8-tetrahydro-5,5,8,8-tetramethylnaphth-2-yl)-propene 1-(4-acetoxyphenyl)-2-(5,6,7,8-tetrahydro-5,5,8,8-tetramethylnaphth-2-yl)-propene 1-(4-propionyloxyphenyl)-2-(5,6,7,8-tetrahydro-5,5,8,8-tetramethylnaphth- 2-yl)-propene 1-(4-palmitoyloxyphenyl)-2-(5,6,7,8-tetrahydro-5,5,8,8-tetramethylnaphth-2-yl)-propene 1-(4-stearoyloxyphenyl)-2-(5,6,7,8-tetrahydro-5,5,8,8-tetramethylnaphth-2-yl)-propene 1-(4-benzoyloxyphenyl)-2-(5,6,7,8-tetrahydro-5,5,8,8-tetramethylnaphth-2-yl)-propene 1-[4-(4-methylbenzoyl)oxyphenyl]-2-(5,6,7,8-tetrahydro-5,5,8,8-tetramethylnaphth-2-yl)-propene 1-[4-(4-methoxybenzoyl)oxyphenyl]-2-(5,6,7,8-tetrahydro-5,5,8,8-tetramethylnaphth-2-yl)-propene 1-[4-(3-chlorobenzoyl)oxyphenyl]-2-(5,6,7,8-tetrahydro-5,5,8,8-tetramethylnaphth-2-yl)-propene 1-(4-benzyloxyphenyl)-2-(5,6,7,8-tetrahydro-5,5,8,8-tetramethylnaphth-2-yl)-propene 1-[4-(4-methoxybenzyl)oxyphenyl]-2-(5,6,7,8-tetrahydro-5,5,8,8-tetramethylnaphth-2-yl)-propene 1-[4-(4-methylbenzyl)oxyphenyl]-2-(5,6,7,8-tetrahydro-5,5,8,8-tetramethylnaphth-2-yl)-propene 1-[4-(3-fluorobenzyl)oxyphenyl]-2-(5,6,7,8-tetrahydro-5,5,8,8-tetramethylnaphth-2-yl)-propene 1-[4-(2-hydroxyethyl)oxyphenyl]-2-(5,6,7,8-tetrahydro-5,5,8,8-tetramethylnaphth-2-yl)-propene 1-[4-(2-methoxyethyl)oxyphenyl]-2-(5,6,7,8-tetrahydro-5,5,8,8-tetramethylnaphth-2-yl)-propene 1-[4-(2,3-dihydroxypropyl)oxyphenyl]-2-(5,6,7,8-tetrahydro-5,5,8,8-tetramethylnaphth-2-yl)-propene 1-[4-(2-aminoethyl)oxyphenyl]-2-(5,6,7,8-tetrahydro-5,5,8,8-tetramethylnaphth-2-yl)-propene 1-[4-(2-N-methylaminoethyl)oxyphenyl]-2-(5,6,7,8-tetrahydro-5,5,8,8-tetramethylnaphth-2-yl)-propene 1-[4-(2-N-ethylaminoethyl)oxyphenyl]-2-(5,6,7,8-tetrahydro-5,5,8,8-tetramethylnaphth-2-yl)-propene 1-[4-(2-N,N-dimethylaminoethyl)oxyphenyl]-2-(5,6,7,8-tetrahydro-5,5,8,8-tetramethylnaphth-2-yl)-propene 1-[4-(2-N,N-dimethylaminoethyl)oxyphenyl]-2-(5,6,7,8-tetrahydro-5,5,8,8-tetramethylnaphth-2-yl)-propene methyl 4-[2-(5,6,7,8-tetrahydro-5,5,8,8-tetramethylnaphth-2-yl)-1-propenyl]-phenoxyacetate ethyl 4-[2-(5,6,7,8-tetrahydro-5,5,8,8-tetramethylnaphth-2-yl)-1-propenyl]-phenoxyacetate 4-[2-(5,6,7,8-tetrahydro-5,5,8,8-tetramethylnaphth-2-yl)-1-propenyl]-phenoxyacetic acid 1-(3,4-dihydroxyphenyl)-2-(5,6,7,8-tetrahydro-5,5,8,8-tetramethylnaphth-2-yl)-propene 1-(3-hydroxy-4-methoxyphenyl)-2-(5,6,7,8-tetrahydro-5,5,8,8-tetramethylnaphth-2-yl)-propene 1-(4-hydroxy-3-methoxyphenyl)-2-(5,6,7,8-tetrahydro-5,5,8,8-tetramethylnaphth-2-yl)-propene 1-(4-ethoxy-3-hydroxyphenyl)-2-(5,6,7,8-tetrahydro-5,5,8,8-tetramethylnaphth-2-yl)-propene 1-(3,4-dimethoxyphenyl)-2-(5,6,7,8-tetrahydro-5,5,8,8-tetramethylnaphth-2-yl)-propene 5-[1-(-2-(5,6,7,8-tetrahydro-5,5,8,8-tetramethylnaphth-2-yl)-1-propenyl]-1,3-benzodioxole 2-methyl-5-[2-(5,6,7,8-tetrahydro-5,5,8,8-tetramethylnaphth-2-yl)-1-propenyl]-1,3-benzodioxole 2,2-dimethyl-5-[2-(5,5,8,8-tetramethylnaphth-2-yl)-1-propenyl]-1,3-benzodioxole
2-phenyl-5-[2-(5,6,7,8-tetrahydro-5,5,8,8-tetramethyl-2-naphth-2-yl)-1-propenyl]-1,3-benzodioxole
2-oxo-5-[2-(5,6,7,8-tetrahydro-5,5,8,8-tetramethyl-naphth-2-yl)-1-propenyl]-1,3-benzodioxole
2-thioxo-5-[2-(5,6,7,8-tetrahydro-5,5,8,8-tetramethyl-naphth-2-yl)-1-propenyl]-1,3-benzodioxole
6-[2-(5,6,7,8-tetrahydro-5,5,8,8-tetramethylnaphth-2-yl)-1-propenyl]-1,4-benzodioxane
1-(4-acetoxy-3-hydroxyphenyl)-2-(5,6,7,8-tetrahydro-5,5,8,8-tetramethylnaphth-2-yl)-propene
1-(4-acetoxy-3-methoxyphenyl)-2-(5,6,7,8-tetrahydro-5,5,8,8-tetramethylnaphth-2-yl)-propene
1-(3,4-diformyloxyphenyl)-2-(5,6,7,8-tetrahydro-5,5,8,8-tetramethylnaphth-2-yl)-propene
1-(3,4-diacetoxyphenyl)-2-(5,6,7,8-tetrahydro-5,5,8,8-tetramethylnaphth- 2-yl)-propene
1-(3,4-dipropionyloxyphenyl)-2-(5,6,7,8-tetrahydro-5,5,8,8-tetramethylnaphth-2-yl)-propene
1-(3,4-dibutyloxyphenyl)-2-(5,6,7,8-tetrahydro-5,5,8,8-tetramethylnaphth-2-yl)-propene
1-(3,4,5-trihydroxyphenyl)-2-(5,6,7,8-tetrahydro-5,5,8,8-tetramethylnaphth-2-yl)-propene
1-(3,4,5-trimethoxyphenyl)-2-(5,6,7,8-tetrahydro-5,5,8,8-tetramethylnaphth-2-yl)-propene
1-(3-hydroxy-4,5-dimethoxyphenyl)-2-(5,6,7,8-tetrahydro-5,5,8,8-tetramethylnaphth-2-yl)-propene
1-(4-hydroxyphenyl)-2-(5,6,7,8-tetrahydro-5,5,8,8-tetramethylnaphth-2-yl)-ethene
1-(4-hydroxyphenyl)-2-(5,6,7,8-tetrahydro-5,5,8,8-tetramethylnaphth-2-yl)-butene
1-(4-hydroxyphenyl)-2-(5,6,7,8-tetrahydro-5,5,8,8-tetramethylnaphth-2-yl)-pentene
1-(4-hydroxyphenyl)-2-(5,6,7,8-tetrahydro-5,5,8,8-tetramethylnaphth-2-yl)-hexene
2-cyclopropyl-1-(4-hydroxyphenyl)-2-(5,6,7,8-tetrahydro-5,5,8,8-tetramethylnaphth-2-yl)-ethene
1-(4-methoxyphenyl)-2-(5,6,7,8-tetrahydro-5,5,8,8-tetramethylnaphth-2-yl)-ethene
1-(4-methoxyphenyl)-2-(5,6,7,8-tetrahydro-5,5,8,8-tetramethylnaphth-2-yl)-butene
1-(4-acetoxyphenyl)-2-(5,6,7,8-tetrahydro-5,5,8,8-tetramethylnaphth-2-yl)-ethene
1-(4-hydroxyphenyl)-2-(5,6,7,8-tetrahydro-5,5,8,8-tetramethylnaphth-2-yl)-propene
1-(4-hydroxyphenyl)-2-(5,6,7,8-tetrahydro-3-methoxy-5,5,8,8-tetramethylnaphth-2-yl)-propene
1-(4-hydroxyphenyl)-2-(3-ethyl-5,6,7,8-tetrahydro-3-methoxy-5,5,8,8-tetramethylnaphth-2-yl)propene
1-(4-hydroxyphenyl)-2-(3-fluoro-5,6,7,8-tetrahydro-3-methoxy-5,5,8,8-tetramethylnaphth-2-yl)propene
1-(4-methoxyphenyl)-2-(5,6,7,8-tetrahydro-5,5,8,8-pentamethylnaphth-2-yl)propene
1-(4-methoxyphenyl)-2-(5,6,7,8-tetrahydro-3-methoxy-5,5,8,8-tetramethylnaphthyl)-propene
1-(4-methoxyphenyl)-2-(3-ethyl-5,6,7,8-tetrahydro-5,5,8,8-tetramethylnaphth-2-yl)-propene
1-(4-methoxyphenyl)-2-(3-fluoro-5,6,7,8-tetrahydro-5,5,8,8-tetramethylnaphth-2-yl)-propene
1-(4-hydroxyphenyl)-2-(2,3-dihydro-1,1,3,3-tetramethyl-5(1H)-indenyl)-propene
1-(4-methoxyphenyl)-2-(2,3-dihydro-1,1,3,3-tetramethyl-(5(1H)-indenyl)-propene
1-(4-acetoxyphenyl)-2-(2,3-dihydro-1,1,3,3-tetramethyl-(5(1H)-indenyl)-propene
1-(4-hydroxyphenyl)-2-(2,3-dihydro-1,1,2,3,3-pentamethyl-(5(1H)-indenyl)-propene
1-(4-methoxyphenyl)-2-(2,3-dihydro-1,1,2,3,3-pentamethyl-(5(1H)-indenyl)-propene
1-(4-acetoxyphenyl)-2-(2,3-dihydro-1,1,2,3,3-pentamethyl-(5(1H)-indenyl)-propene
1-(4-hydroxyphenyl)-2-(5,6,7,8-tetrahydro-3,8,8,-trimethylnaphth-2-yl)-propene
1-(4-methoxyphenyl)-2-(5,6,7,8-tetrahydro-3,8,8-trimethylnaphth-2-yl)-propene
1-(4-acetoxyphenyl)-2-(5,6,7,8-tetrahydro-3,8,8-trimethylnaphth-2-yl)-propene The compounds according to the invention can be prepared by various methods, each of which is known in principle. For example, a carbonyl compound of the formula II

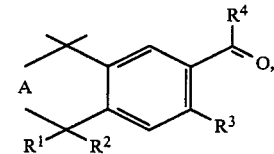

where A, $R^1$, $R^2$, $R^3$ and $R^4$ have the stated meanings, can be subjected to a Wittig-Horner reaction with a phosphorus compound of the formula III

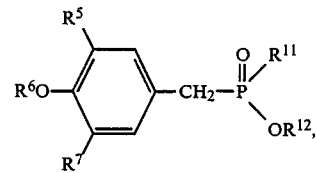

where $R^5$, $R^6$ and $R^7$ have the stated meanings and $R^{11}$ and $R^{12}$ are each $C_1$-$C_3$-alkyl. Advantageously, the reaction is carried out in a solvent in the presence of a basic compound usually employed for Wittig-Horner reactions.

The Wittig-Horner reaction is carried out at from −20° to 100° C., advantageously from 20° to 50° C., under atmospheric pressure or in a closed vessel under superatmospheric pressure, if necessary the mixture being heated to the stated temperature.

This reaction can be carried out in the presence of a diluent or solvent, for example a lower saturated dialkyl ether, dialkyl glycol ether or cyclic ether, such as diethyl ether, ethyl tert-butyl ether, 1,2-dimethoxy ethane, tetrahydrofuran or dioxane, an aromatic hydrocarbon, such as benzene or an alkyl benzene such as toluene or xylene, a saturated aliphatic hydrocarbon, such as hexane, heptane or isooctane, a lower aliphatic ketone, such as acetone, methyl ethyl ketone or methyl isobutyl ketone, a dialkylformamide, such as dimethyl- or diethylformamide, or a mixture of the stated solvents. Cyclic ethers, such as dioxane or tetrahydrofuran, and in particular dimethylformamide or mixtures of these are preferably used, the reaction generally being carried out at from 0° to 30° C.

The reactions are carried out in the presence of a deprotonating agent for the phosphonate (III). Alkali metal hydrides and alkali metal amides, in particular those of sodium and potassium, the sodium and potassium salts of dimethyl sulfoxide, alkyllithium compounds, such as n-butyllithium, and alkali metal alcoholates, preferably sodium ethanolate and sodium methalate, are suitable.

The compounds according to the invention can also be obtained by subjecting a phosphonium salt of the formula IV

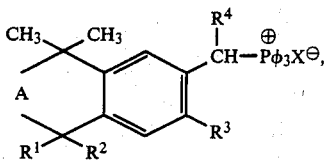

where A, $R^1$, $R^2$, $R^3$ and $R^4$ have the above meanings and $X^\ominus$ is an anion, preferably chlorine or bromine, to a Wittig reaction with a benzaldehyde of the formula V

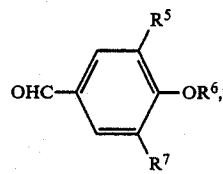

where $R^5$, $R^6$ and $R^7$ have the stated meanings.

The Wittig or Wittig-Horner reaction usually gives mixtures of the steric (E/Z) olefin isomers.

E/Z isomer mixtures predominantly containing the Z isomer undergo rearrangement at the olefinic double bond in the presence of light to give mixtures having a higher content of the (E) isomer. Pure (E) compounds of the formula (I) are advantageously obtained from the resulting (E/Z) isomer mixtures which now have a more favorable (E) content, preferably by crystallization or a chromatographic method, such as column chromatography or preparative HPLC.

Carboxylates of the general formula I can, if desired, be converted to the free carboxylic acids or to the free phenols and their physiologically tolerated salts by ester hydrolysis. Advantageously, the hydrolysis is carried out in the presence of a diluent, for example a water-miscible ether, such as 1,2-dimethoxyethane or tetrahydrofuran, or a lower aliphatic alcohol, such as methanol, ethanol, propanol, isopropanol or butanol, in the presence or absence of water or in a mixture of the stated solvents with water. Preferred solvents are aqueous mixtures of ethanol or methanol, the reaction being carried out at from 20° C. to the boiling point of the reaction mixture. The hydrolysis is preferably carried out in the presence of a hydroxide or carbonate of an alkali metal or alkaline earth metal, in particular of sodium or potassium.

Conversely, a carboxylic acid of the formula I can be esterified in a conventional manner. For example, the carboxylic acid can be converted to the corresponding acyl chloride in the presence of an inorganic acid chloride, preferably thionyl chloride, and the said acyl chloride can then be reacted with the desired alcohol, a large excess of the alcohol advantageously being used and, if necessary, the reaction being carried out in an inert solvent, for example a hydrocarbon, such as toluene. In some cases, it has also proven advantageous to add a tertiary nitrogen base, such as triethylamine or pyridine, in order to bind the hydrogen halide formed.

The esterification can also be carried out advantageously if the carboxylic acid is first converted to its salt and the latter treated with an appropriate alkyl halide, preferably an alkyl bromide or iodide. Suitable deprotonating agents for the preparation of the salts in situ are, in particular, the carbonates, hydroxides and hydrides of the alkali metals. Aprotic polar solvents, such as acetone, dimethylformamide, dimethyl sulfoxide and in particular methyl ethyl ketone are advantageously used, the reaction being carried out at the boiling point of the reaction mixture.

A phenol of the formula I can be converted to the esters according to the invention in a conventional manner with an alkanoyl halide or anhydride, an aralkanoyl halide or anhydride or an aroyl halide or anhydride, advantageously in an inert diluent or solvent, for example a lower aliphatic ketone, such as acetone, methyl ethyl ketone or methyl isobutyl ketone, or a dialkylformamide, such as dimethylformamide or diethylformamide, or with excess acylating agent as a diluent or solvent. The reaction is preferably carried out in the presence of a base as an acid acceptor, at from −20° C. to the boiling point of the reaction mixture. The suitable bases are alkali metal carbonates, bicarbonates, hydroxides and alcoholates, in particular those of sodium and potassium, basic oxides, such as alumina and calcium oxide, tertiary organic bases, such as pyridine or lower trialkylamines, eg. trimethylamine or triethylamine. In relation to the alkylating agent employed, the bases can be used in a catalytic amount, a stoichiometric amount or a slight excess.

The etherification of the phenols of the formula I to give aryl ethers of the formula I is advantageously carried out by first converting the phenol to its salt and then treating the latter with an appropriate alkyl halide or sulfate, preferably an alkyl chloride, bromide or iodide. Suitable deprotonating agents for the preparation of the phenolates in situ are, in particular, the carbonates, hydroxides and hydrides of the alkali metals. Aprotic polar solvents, such as acetone, dimethylformamide, dimethyl sulfoxide or methyl ethyl ketone, are advantageously used, the reaction being carried out at from 20° C. to the boiling point of the reaction mixture.

Pyrocatechol derivatives of the formula I (where $R^5$ is OH and $R^6$ is H) can be converted to the corresponding carbonates or thiocarbonates with phosgene or thiophosgene by the procedure described above for the acylation of phenols.

Furthermore, pyrocatechol derivatives of the formula I (where $R^5$ is OH and $R^6$ is H) can be converted with ketones or aldehydes in a conventional manner to the corresponding benzodioxole derivatives. The reaction is advantageously carried out in the presence of an acid as a catalyst, and the water formed during the reaction is removed by azeotropic distillation using a water separator. Mineral acids, such as hydrochloric acid and sulfuric acid, and organic acids, in particular sulfonic acids, eg. benzene sulfonic and toluene sulfonic acid, are used as acids. As is usual in this type of reaction, solvents such as toluene, benzene, saturated hydrocarbons, eg. petroleum ether, or chlorohydrocarbons, eg. chloroform or carbon tetrachloride, are employed as water entrainers. An excess of the ketone or aldehyde is advantageous.

Some of the novel compounds have an acidic hydrogen atom and can therefore be converted with the bases in a conventional manner to a physiologically tolerated, readily water-soluble salt. Examples of suitable salts are ammonium salts, alkali metal salts, in particular those of sodium, potassium and lithium, alkaline earth metal salts, in particular those of calcium and magnesium, and salts with suitable organic bases, such as lower alkylamines eg. methylamine, ethylamine or cyclohexylamine, or substituted alkylamines, such as diethanolamine, triethanolamine or tris-(hydroxymethyl)-aminomethane, as well as with piperidine or morpholine.

If necessary, the novel amines of the formula (I) which are obtained are converted by a conventional procedure to an addition salt of a physiologically tolerated acid. Examples of conventional physiologically tolerated inorganic acids are hydrochloric acid, hydrobromic acid, phosphoric acid and sulfuric acid, and examples of conventional organic acids are oxalic acid, maleic acid, fumaric acid, lactic acid, tartaric acid, malic acid, citric acid, salicylic acid, adipic acid and benzoic acid. Other examples are described in Fortschritte der Arzneimittelforschung, Volume 10, pages 224–225, Birkhäuser Verlag, Basel and Stuttgart, 1966.

Because of their pharmacological properties, the novel compounds and their physiologically tolerated salts can be used for the topical and systemic therapy and the prophylaxis of precancers and carcinomas of the skin, the mucous membranes and internal organs and for the topical and systemic therapy of acne, psoriasis and other disorders with pathologically changed keratinization, and of rheumatic disorders, in particular those of an inflammatory or degenerative nature, which affect joints, muscles, tendons, and other parts of the apparatus of locomotion. In addition to the therapy of dermatological disorders, a preferred indication is the prophylactic and therapeutic treatment of precancers and tumors.

The pharmacological actions can be demonstrated, for example, in the following test models. The compounds according to the invention eliminate the keratinization which sets in after vitamin A deficiency in in vitro hamster tracheal tissue. Keratinization forms part of the early phase of carcinogenesis, which is inhibited in vivo by the novel compounds of the formula (I) by a similar technique after initiation by chemical compounds, by high energy radiation or after viral cell transformation. These methods are described in Cancer Res. 36 (1976), 964–972, Nature 250 (1974) 64–66, ibid. 253 (1975) 47–50 and Cancer Res. 43 (1983), 24,695.

Furthermore, the novel compounds inhibit the proliferation rates of certain malignant cells. These methods are described in J. Natl. Cancer Inst. 60 (1978), 1035–1041, Experimental Cell Research 117 (1978), 15–22, and Proc. Natl. Acad. Sci., USA 77 (1980), 2937–2940.

The antiarthritic action of the compounds according to the invention can be determined in a conventional manner in an animal experiment using the adjuvant arthritis model or the Streptococci cell wall-induced arthritis model. This method is described in, for example, "Retinoids, differentiation and disease, Ciba Foundation Symposium 113, pages 191–211, Pitman, London, 1985.

The dermatological activity, for example for the treatment of acne, can be demonstrated, inter alia, by the komedolytic activity and the ability to reduce the number of cysts in the rhino mouse model.

This method is described by L. H. Kligman et al. in the Journal of Investigative Dermatology 73 (1978), 354–358.

Accordingly, the present invention furthermore relates to therapeutic agents for topical and systemic use, which contain a compound of the formula (I) as the active compound in addition to conventional carriers or diluents, and the use of a compound of the formula (I) for the preparation of a drug.

The therapeutic agents or formulations are prepared using the conventional liquid or solid carriers or diluents and the conventionally used pharmaceutical auxiliaries, in accordance with the desired route of administration and in a dose suitable for administration, in a conventional manner, for example by mixing the active compound with the solid or liquid carriers and auxiliaries conventionally used in such preparations.

Accordingly, the agents can be administered orally, parenterally or topically. Examples of formulations of this type are tablets, film tablets, coated tablets, capsules, pills, powders, solutions and suspensions, infusion and injectable solutions, as well as pastes, ointments, gels, creams, lotions, dusting powders, solutions or emulsions and sprays.

The therapeutic agents may contain the compounds used according to the invention in a concentration of from 0.001 to 1%, preferably from 0.001 to 0.1%, for local administration, and preferably in a single dose of from 0.1 to 50 mg for systemic administration, and may be administered in one or more doses daily, depending on the type and severity of the disorders.

Examples of pharmaceutical auxiliaries which are usually employed are alcohols, such as isopropanol, oxyethylated castor oil or oxyethylated hydrogenated castor oil, polyacrylic acid, glycerol monostearate, liquid paraffin, vaseline, woolfat, polyethylene glycol 400, polyethylene glycol 400 stearate and oxyethylated fatty alcohol, for local administration, and lactose, propylene glycol, ethanol, starch, talc and polyvinylpyrrolidone for systemic administration. If necessary, an antioxidant, eg. tocopherol or butylated hydroxyanisole or butylated hydroxy toluene, or flavor-improving additives, stabilizers, emulsifiers, lubricants, etc. may be added to the preparations. All substances used in the oreparation of pharmaceutical formulations must be toxicologically acceptable and compatible with the active compounds used.

EXAMPLE 1

Method A:

(E)-1-(4-methoxyphenyl)-2-(5,6,7,8-tetrahydro-5,5,8,8-tetramethylnaphth-2-yl)-propene A solution of 100.4 g (0.18 mole) of 1-(5,6,7,8-tetrahydro-5,5,8,8-tetramethylnaohth-2-yl)-ethyltriphenylohosphonium bromide in 300 ml of absolute dimethylsulfoxide was added dropwise at from 40° to 45° C. to a suspension of 6 g (0.2 mole) of sodium hydride (80% strength, freed beforehand from the 20% paraffin portion with petroleum ether) in 200 ml of absolute tetrahydrofuran. Stirring was continued until the evolution of gas was complete, which took 0.5 h, after which a further 50 ml of tetrahydrofuran were added and a solution of 21.7 g (0.16 mole) of 4-methoxybenzaldehyde in 80 ml of tetrahydrofuran was added dropwise in the course of 20 minutes at about 30° C. Stirring was continued overnight, after which the mixture was poured onto 1 l of water and extracted three times with ether. The combined ether phases were washed once with water, dried over $Na_2SO_4$ and evaporated down. The semicrystalline residue (102.0 g) in 600 ml of n-heptane was heated at the boil and left to cool again. The solid (mainly triphenylphosphine oxide) was filtered off, and the filtrate was evaporated down. The residue was recrystallized from 550 ml of methanol. When the product was dried, 26.4 g of the title compound of melting point 103°-104° C. were obtained.

Method B:

11.5 g (0.1 mole) of potassium tert-butylate were added a little at a time to a solution of 26.3 g (0.1 mole) of diethyl p-methoxybenzylphosphonate in 400 ml of absolute dimethylformamide under nitrogen and at room temperature. Stirring was continued for 30 minutes, after which a solution of 11.5 g (0.05 mole) of 2-acetyl-5,6,7,8-tetrahydro-5,5,8,8-tetramethylnaphthalene in 100 ml of absolute dimethylformamide was added dropwise at room temperature. The mixture was then stirred for 4 hours at 60° C. and again for 4 hours at 80° C. After cooling, the mixture was poured onto 1 of ice water and extracted with three times 80 ml of ether. To facilitate extraction the mixture was acidified. The combined ether extracts were washed with five times 200 ml of $H_2O$, dried over $MgSO_4$ and evaporated down. The residue was stirred with methanol and left to stand at $-20°$ C. (freezer compartment). On the next day, the crystals were filtered off under suction and dried to give 6 g of the title compound, which, on the basis of physical data, was identical to the compound prepared by method A.

EXAMPLE 2

(E)-1-(4-butoxyphenyl)-2-(5,6,7,8-tetrahydro-5,5,8,8-tetramethylnaphth-2-yl)-propene A method similar to that described in Example 1 was used, and 11.5 g of the title compound of melting point 107°-108° C. were obtained from 6 g (0.2 mole) of 80% strength sodium hydride, 100.4 g (0.18 mole) of 1-(5,6,7,8-tetrahydro-5,5,8,8-tetramethylnaphth-2-yl)-ethyltriphenylphosphonium bromide and 28.5 g (0.16 mole) of 4-tert-butoxybenzaldehyde. The crude crystals remaining after extraction with heptane were prepurified by means of flash chromatography (150 g of silica gel 60, 60-230 mesh; n-heptane) and finally recrystallized from 1:8 tetrahydrofuran/ethanol/methanol.

EXAMPLE 3

(E)-5-[2-(5,6,7,8-tetrahydro-5,5,8,8-tetramethyl-naphth-2-yl)-1-propenyl]-1,3-benzodioxole A method similar to that described in Example 1 was used and 4.3 g of the title compound of melting point 90°-91° C. were obtained from 1.5 g (0.05 mole) of 80% strength sodium hydride, 25.1 g (0.045 mole) of 1-(5,6,7,8-tetrahydro-5,5,8,8-tetramethylnaphth-2-yl)ethyltriphenylphosphonium bromide and 6.0 g (0.04 mole) of piperonal.

EXAMPLE 4

Ethyl (E)-4-[2-(5,6,7,8-tetrahydro-5,5,8,8-tetramethylnaphth-2-yl)-1-propenyl]-phenoxyacetate A method similar to that described in Example 1 was used and 2.5 g of the title compound of melting point 71°-73° C. were obtained from 1.5 g (0.05 mole) of 80% strength sodium hydride, 25.1 g (0.045 mole) of 1-(5,6,7,8-tetrahydro-5,5,8,8-tetramethylnaphth-2-yl)ethyltriphenylphosphonium bromide and 8.3 g (0.04 mole) of ethyl 4-formylphenoxy acetate. The oily crude product which remained after extraction with heptane was prepurified by means of flash chromatography (200 g of silica gel 60, 230-400 mesh; n-heptane+1% of ethylacetate) and finally recrystallized from 1:3 methanol/ethanol.

EXAMPLE 5

(E)-1-(3,4-diacetoxyphenyl)-2-(5,6,7,8-tetrahydro-5,5,8,8-tetramethylnaphth-2-yl)-propene A method similar to that described in Example 1 was used and 7.0 g of the title compound of melting ooint 135°-137° C. were obtained from 3.0 g (0.1 mole) of 80% strength sodium hydride, 50.4 g (0.09 mole) of 1-(5,6,7,8-tetrahydro-5,5 8,8-tetramethylnaphth-2-yl)ethyl-triphenylphosphonium bromide and 15.2 g (0.08 mole) of 3,4-diacetoxybenzaldehyde.

EXAMPLE 6

(E)-1-(4-hydroxyphenyl)-2-(5,6,7,8-tetrahydro-5,5,8,8-tetramethylnaphth-2-yl)-propene 3.8 g (11 mmol) of (E)-1-(4-methoxyphenyl)-2-(5,6,7,8-tetrahydro-5,5,8,8-tetramethylnaphth-2-yl)-propene from Example 1 were suspended in 50 ml of methanol saturated with hydrogen chloride, and the suspension was stirred for 20 minutes at 60° C. Thereafter, the reaction solution was poured into about 150 ml of ice water and extracted with three times 100 ml of methyl tert-butyl ether. The organic phase was washed with twice 100 ml of saturated sodium chloride solution and twice with water, dried over $Na_2SO_4$ and evaporated down to give 4 g of a solid crude product. This crude product was recrystallized from isopropanol to give 1.5 g of the title compound of melting point 138°-140° C.

EXAMPLE 7

(E)-4-[2-(5,6,7,8-tetrahydro-5,5,8,8-tetramethyl-naphth-2-yl)-1-propenyl]phenoxy acetic acid 1.6 g (4 mmol) of ethyl (E)-4-[2-(5,6,7,8-tetrahydro-5,5,8,8-tetramethylnaphth-2-yl)-1-propenyl]-phenoxy acetate from Example 4 and 0.5 g (8 mmol) of 85% strength potassium hydroxide in a mixture of 20 ml of ethanol and 1 ml of water were refluxed for 1 hour. Thereafter, the mixture was allowed to cool, poured onto 100 ml of water and acidified with dilute HCl. After some time, crystals formed; they were filtered off under suction, washed with water and a little ice-cold methanol and dried to give 1.2 g of the title compound of melting point 152°-154° C.

We claim:

1. A vinylphenol derivative of the formula I

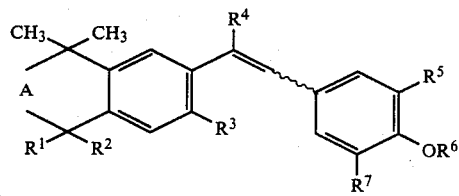

where

A is a methylene or ethylene radical which is unsubstituted or substituted by $C_1$-$C_4$-alkyl, $R^1$ and $R^2$ are each hydrogen or methyl, $R^3$ is hydrogen, $C_1$-$C_4$-alkyl, $C_1$-$C_4$-alkoxy or halogen, $R^4$ is hydrogen, $C_1$-$C_4$-alkyl, cyclopropyl or cyclobutyl, $R^5$ and $R^7$ are each hydrogen or $-OR^8$, where $R^8$ is hydrogen, $C_1$-$C_4$-alkyl or $C_1$-$C_4$-alkanoyl, and $R^6$ is hydrogen or is $C_1$-$C_4$-alkyl which is unsubstituted or substituted by carboxyl, $C_1$-$C_4$-alkoxycarbonyl, hydroxyl, $C_1$-$C_4$-alkoxy and/or amino or mono- or di-$C_1$-$C_4$-alkylamino, or is $C_1$-$C_{20}$-alkanoyl or is benzoyl which is unsubstituted or substituted as described for the $C_1$-$C_4$-alkyl group, or is aralkyl which is unsubstituted or similarly substituted in the aryl moiety, and $R^6$ and $R^8$ together may furthermore form a radical C=O, C=S, —CH$_2$CH$_2$— or $CR^9R^{10}$, where $R^9$ and $R^{10}$ are each hydrogen, $C_1$-$C_4$-alkyl or phenyl, and its physiologically tolerated salts.

2. (E)-1-(4-methoxyphenyl)-2-(5,6,7,8-tetrahydro-5,5,8,8-tetramethylnaphth-2-yl)-propene 3. (E)-1-(4-hydroxyphenyl)-2-(5,6,7,8-tetrahydro-5,5,8,8-tetramethylnaphth-2-yl)-propene 4. A vinylphenol derivative as claimed in claim 1, as a drug.

5. A drug for topical or systemic control of acne, psoriasis and other dermatological disorders accompanied by pathologically changed keratinization, and of precancers and carcinomas of the skin, the mucous membranes and the internal organs and for the treatment of rheumatic disorders, which contains, in addition to conventional pharmaceutical auxiliaries, an effective amount of a vinylphenol derivative as claimed in claim 1, as active compound.

6. A process for the preparation of a drug for topical or systemic control of acne, psoriasis and other dermatological disorders accompanied by pathologically changed keratinization, and of precancers and carcinomas of the skin, the mucous membranes and the internal organs, and for the treatment of rheumatic disorders, by mixing a vinylphenol derivative as claimed in claim 1, in an amount sufficient for the particular purpose, with conventional pharmaceutical auxiliaries.

* * * * *

UNITED STATES PATENT AND TRADEMARK OFFICE
CERTIFICATE OF CORRECTION

PATENT NO. : 4,714,786
DATED : December 22, 1987
INVENTOR(S) : Hans-Heiner WUEST et al.

It is certified that error appears in the above-identified patent and that said Letters Patent is hereby corrected as shown below:

The Title Items [19] and [75] "Wuesi" should read

-- Wuest --.

Signed and Sealed this

Third Day of May, 1988

*Attest:*

DONALD J. QUIGG

*Attesting Officer*      *Commissioner of Patents and Trademarks*